US009388122B2

(12) United States Patent
Sato et al.

(10) Patent No.: US 9,388,122 B2
(45) Date of Patent: Jul. 12, 2016

(54) RADIOACTIVE TYROSINE DERIVATIVE, METHOD FOR PRODUCING SAME, LABELING AGENT FOR POSITRON IMAGING AND MEDICAL AGENT FOR ASSESSING GRADE OF MALIGNANCY OF TUMOR RESPECTIVELY COMPOSED OF RADIOACTIVE TYROSINE DERIVATIVE, AND METHOD FOR DETECTING TUMOR

(75) Inventors: Kengo Sato, Hamamatsu (JP); Hideo Tsukada, Hamamatsu (JP)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 2262 days.

(21) Appl. No.: 11/597,557

(22) PCT Filed: May 25, 2005

(86) PCT No.: PCT/JP2005/009530
§ 371 (c)(1),
(2), (4) Date: Mar. 11, 2008

(87) PCT Pub. No.: WO2005/115971
PCT Pub. Date: Dec. 8, 2005

(65) Prior Publication Data
US 2008/0138281 A1 Jun. 12, 2008
US 2009/0098048 A2 Apr. 16, 2009

(30) Foreign Application Priority Data

May 28, 2004 (JP) ................. P2004-159941

(51) Int. Cl.
C07C 229/36 (2006.01)
A61K 51/04 (2006.01)
C07B 59/00 (2006.01)

(52) U.S. Cl.
CPC .............. *C07C 229/36* (2013.01); *A61K 51/04* (2013.01); *C07B 59/001* (2013.01); *C07B 2200/05* (2013.01)

(58) Field of Classification Search
CPC .............................. C07C 229/36; A61K 51/04
See application file for complete search history.

(56) References Cited

PUBLICATIONS

Wester et al, The Journal of Nuclear Medicine, 1999, vol. 40, No. 1, pp. 205-212.*
Sirkku Leskinen-Kallio et al., "Uptake of Carbon-11-Methionine and Fluorodeoxyglucose in Non-Hodgkin's Lymphoma: A PET Study", The Journal of Nuclear Medicine, 1991, pp. 1211-1218, vol. 32 No. 6.
Ren Iwata et al., "Radiosynthesis of O-[$^{11}$C]Methyl-$_L$-Tyrosine and O-[$^{18}$F]Fluoromethyl-$_L$-Tyrosine as Potential PET Tracers for Imaging Amino Acid Transport", Journal of Labelled Compounds and Radiopharmaceuticals, 2003, pp. 555-566, vol. 46, John Wiley & Sons, Ltd.
Ren Iwata et al., "[$^{18}$F]Fluoromethyl Triflate, A Novel and Reactive [$^{18}$F]Fluoromethylating Agent: Preparation and Application to the On-Column Preparation of [$^{18}$F]Fluorocholine", Applied Radiation and Isotopes, 2002, pp. 347-352, vol. 57, Elsevier Science Ltd.
Bengt Langstrom et al. "Synthesis of $_L$- and $_D$-[Methyl-$^{11}$C]Methionine", The Journal of Nuclear Medicine, Jun. 1987, pp. 1037-1040, vol. 28, No. 6.
K. Hamacher et al., "Efficient Stereospecific Synthesis of No-Carrier-Added 2-[$^{18}$F]-Fluoro-2-Deoxy-$_D$-Glucose Using Aminopolyether Supported Nucleophilic Substitution", The Journal of Nuclear Medicine, Feb. 1986, pp. 235-238, vol. 27, No. 2.
Toshihiko Hara et al., "PET Imaging of Brain Tumor With [*methyl-$^{11}$C*]Choline", The Journal of Nuclear Medicine, Jun. 1997, pp. 842-847, vol. 38, No. 6.
H.-J. Machulla et al., "Simplified Labeling Approach for Synthesizing 3'-Deoxy-3'—[$^{18}$F]Fluorothymidine ([$^{18}$F]FLT)", Journal of Radioanalytical and Nuclear Chemistry, 2000, pp. 843-846, vol. 243, No. 3, Akademiai Kiado, Budapest Khuwer Academic Publishers, Dordrecht.
Kiichi Ishiwata et al., "Automated Synthesis of Radiochemically Pure $^{11}$C-Labeled Ethyl, Propyl and Butyl Iodides", Applied Radiation and Isotopes, 1999, pp. 693-697, vol. 50, Elsevier Science Ltd.
Norihiro Harada et al., "Potential of [$^{18}$F]β-CFT-FE (2β-Carbomethoxy-3β-(4-Fluorophenyl)-8-(2-[$^{18}$F]Fluoroethyl)Nortropane) as a Dopamine Transporter Ligand: A PET Study in the Conscious Monkey Brain", Synapse, 2004, pp. 37-45, vol. 54, Wiley-Liss, Inc.
Atsushi Takeda et al., "Biological Evaluation of Radiolabeled $_D$-Methionine as a Parent Compound in Potential Nuclear Imaging", Radioisotopes, 1984, pp. 213-217, vol. 33.
Karl-J. Langen et al., "3-[$^{123}$I]Iodo-α-Methyltyrosine and [Methyl-$^{11}$C]-L-Methionine Uptake in Cerebral Gliomas: A Comparative Study Using Spect and PET", The Journal of Nuclear Medicine, 1997, pp. 517-522, vol. 38, No. 4.
Ganghua Tang et al., "Automated Commercial Synthesis System for Preparation of O-(2-[$^{18}$F]Fluoroethyl)-L-Tyrosine by Direct Nucleophilic Displacement on a Resin Column", Journal of Labelled Compounds and Radiopharmaceuticals, 2003, pp. 661-668, vol. 46, John Wiley & Sons Ltd.

(Continued)

*Primary Examiner* — Sudhakar Katakam
(74) *Attorney, Agent, or Firm* — Drinker Biddle & Reath LLP

(57) ABSTRACT

It is intended to provide a radioactive tyrosine derivative represented by the formula (I) or a pharmaceutically acceptable salt thereof:

[Chemical formula 1]

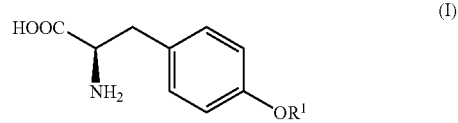

wherein $R^1$ represents a group selected from the group consisting of —$^{11}CH_3$, —$^{11}CH_2CH_3$, —$CH_2{}^{18}F$, and —$CH_2CH_2{}^{18}F$.

1 Claim, 13 Drawing Sheets

(56) References Cited

PUBLICATIONS

S. Leskinen-Kallio et al., "Uptake of $^{11}$C-Methionine in Breast Cancer Studied by PET. An Association With the Size of S-Phase Fraction", Br. J. Cancer, 1991, pp. 1121-1124, vol. 64, Macmillan Press Ltd.

Ganghua Tang et al., "Fully Automated Synthesis of O-(3-[$^{18}$F]Fluoropropyl)-L-Tyrosine by Direct Nucleophilic Exchange on a Quaternary 4-Aminopyridinium Resin", Applied Radiation and Isotopes, 2003, pp. 685-689, vol. 58, Elsevier Science Ltd.

Ganghua Tang et al., "Synthesis and Evaluation of O-(3-[$^{18}$F]Fluoropropyl)-L-Tyrosine as an Oncologic PET Tracer", Nuclear Medicine and Biology, 2003, pp. 733-739, vol. 30, No. 7, Elsevier Inc.

Kiichi Ishiwata et al., "Evaluation of O-[$^{11}$C]Methyl-L-Tyrosine and O-[$^{18}$F]Fluoromethyl-L-Tyrosine as Tumor Imaging Tracers by PET", Nuclear Medicine and Biology 2004, pp. 191-198, vol. 31, No. 2, Elsevier Inc.

A. Van Langevelde et al., "Potential Radiopharmaceuticals for the Detection of Ocular Melanoma Part III. A Study With $^{14}$C and $^{11}$C Labelled Tyrosine and Dihydroxyphenylalanine", European Journal of Nuclear Medicine, 1988, pp. 382-387, vol. 14, No. 7-8, Springer-Verlag.

John M. Bolster et al., "Carbon-11 Labelled Tyrosine to Study Tumor Metabolism by Positron Emission Tomography (PET)", European Journal of Nuclear Medicine, 1986, pp. 321-324, vol. 12, No. 7, Springer-Verlag.

Hans J. Wester et al., "Synthesis and Radiopharmacology of O-(2-[$^{18}$F]Fluoroethyl)-$_L$-Tyrosine for Tumor Imaging", The Journal of Nuclear Medicine, Jan. 1999, pp. 205-212, vol. 40, No. 1, the Official Publication of the Society of Nuclear Medicine, Inc.

Peter Heiss et al., "Investigation of Transport Mechanism and Uptake Kinetics of O-(2-[$^{18}$F]Fluoroethyl)-L-Tyrosine In Vitro and In Vivo", The Journal of Nuclear Medicine, Aug. 1999, pp. 1367-1373, vol. 40, No. 8.

Database Crossfire Beilstein, Beilstein Institute Zur Foerderung Der Chemischen Wissenschaften, XP-002576011, Journal of Labelled Compounds and Radiopharmaceuticals, vol. 46, No. 6, 2003, pp. 555-566, Accession No. 9483903.

Database Crossfire Beilstein, Beilstein Institute Zur Foerderung Der Chemischen Wissenschaften, XP-002576012, Journal of Labelled Compounds and Radiopharmaceuticals, vol. 46, 2003, pp. S135-S135, Accession No. 9488212.

Database Crossfire Beilstein, Beilstein Institute Zur Foerderung Der Chemischen Wissenschaften, XP-002576013, Journal of Labelled Compounds and Radiopharmaceuticals, vol. 46, No. 7, 2003, 661-668, Accession No. 8843774.

\* cited by examiner

Fig. 1
(a)
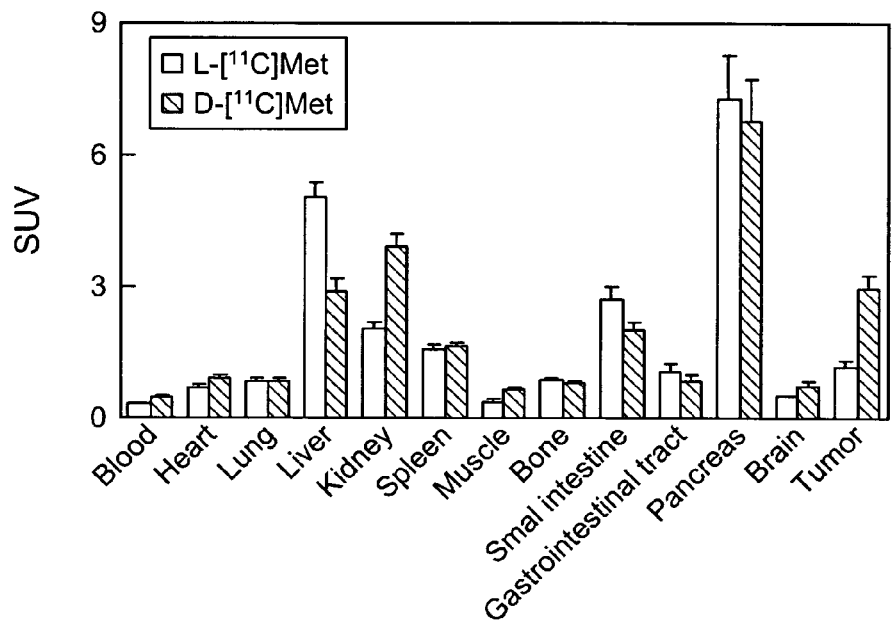
(b)
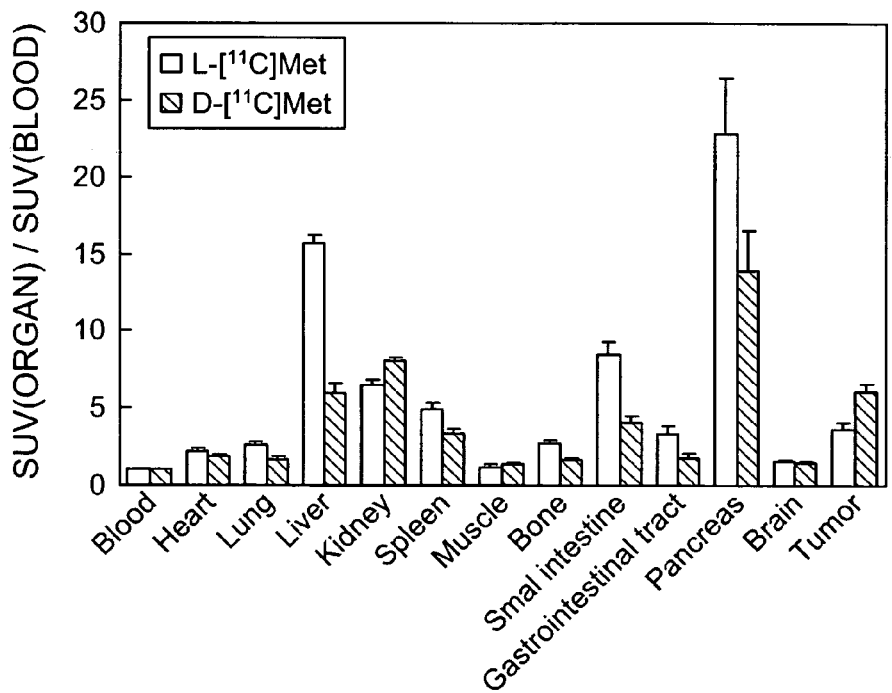

*Fig.2*
(a)
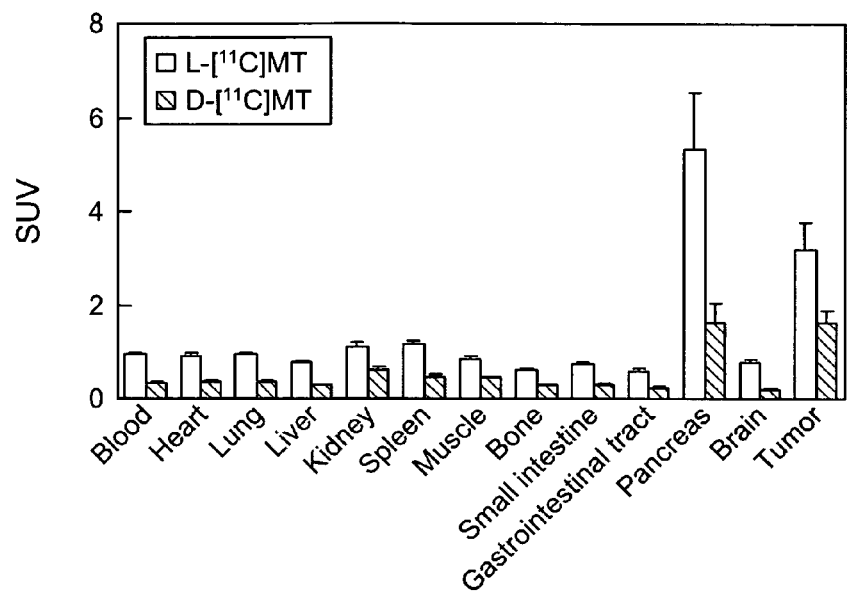
(b)
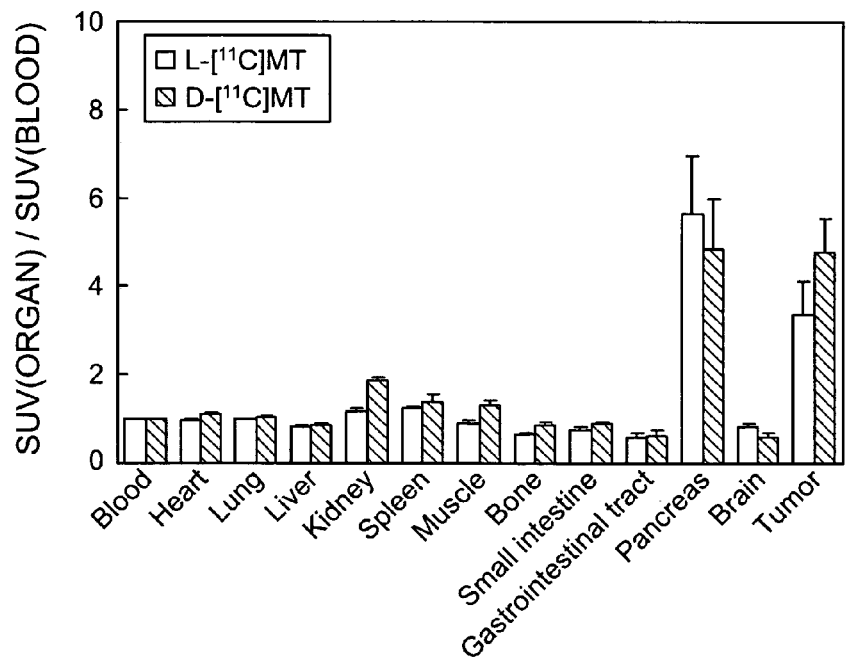

*Fig.3*
(a)
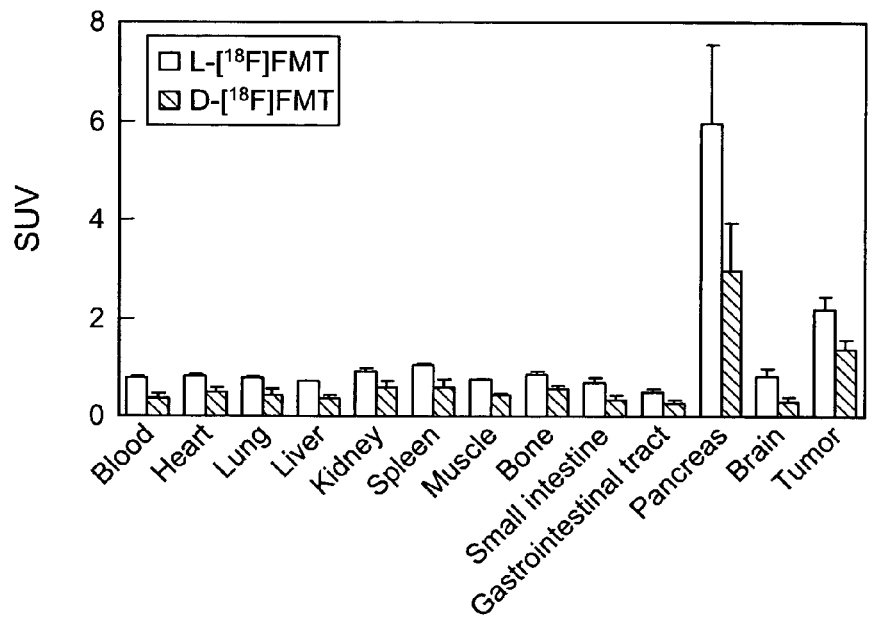
(b)
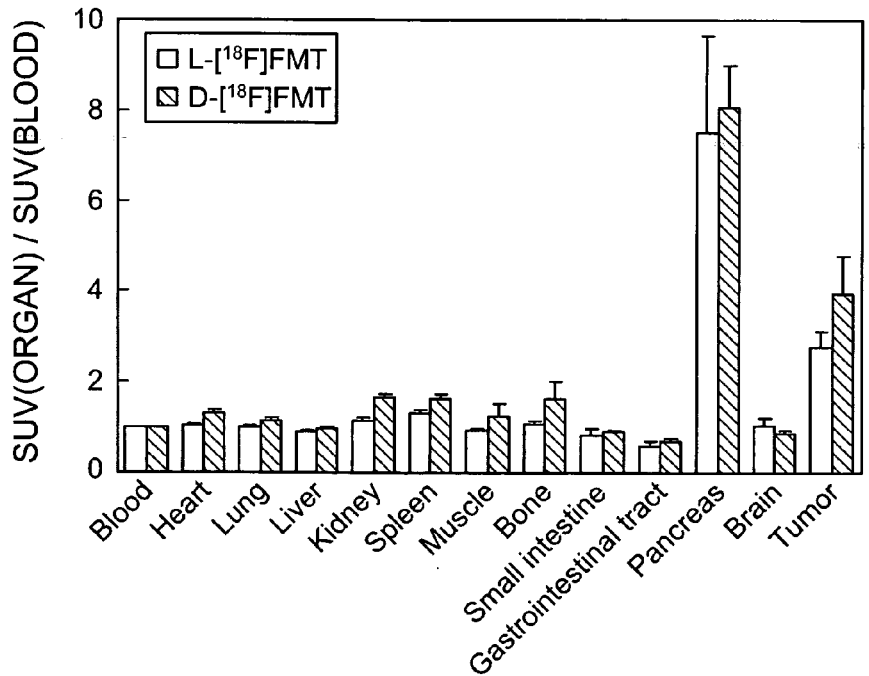

RADIOACTIVE TYROSINE DERIVATIVE, METHOD FOR PRODUCING SAME, LABELING AGENT FOR POSITRON IMAGING AND MEDICAL AGENT FOR ASSESSING GRADE OF MALIGNANCY OF TUMOR RESPECTIVELY COMPOSED OF RADIOACTIVE TYROSINE DERIVATIVE, AND METHOD FOR DETECTING TUMOR

TECHNICAL FIELD

The present invention relates to a radioactive tyrosine derivative, a method for producing same, a labeled agent for positron imaging and an agent for assessing grade of tumor malignancy respectively consisting of a radioactive tyrosine derivative, and a method for detecting tumor.

BACKGROUND ART

Tumor diagnosis by PET (positron emission tomography) exploits the phenomenon where tumor tissues proliferate rapidly as compared with normal tissues. For example, [$^{18}$F]-2-fluoro-2-deoxy-D-glucose (hereinafter, abbreviated to [$^{18}$F]FDG), which is most widely used clinically at present, is a glucose analog, and its use in the diagnosis is based on the fact that the localization of [$^{18}$F]FDG reflects energy metabolism. Alternatively, L-[$^{11}$C]methionine (hereinafter, abbreviated to L-[$^{11}$C]Met), a derivative of a natural amino acid, is also used in tumor diagnosis by PET, which utilizes the fact that the localization of L-[$^{11}$C]Met reflects amino acid metabolism (see e.g., Non-Patent Document 1).

[Non-Patent Document 1] The Journal of Nuclear Medicine, 1991, Vol. 32, No. 6, p. 1211-1218

[Non-Patent Document 2] The Journal of Nuclear Medicine, 1999, Vol. 40, No. 1, p. 205-212

[Non-Patent Document 3] The Journal of Nuclear Medicine, 1999, Vol. 40, No. 8, p. 1367-1373

DISCLOSURE OF THE INVENTION

Problem to be Solved by the Invention

However, since [$^{18}$F]FDG also accumulates in inflammatory sites and so on, its specificity to tumor is not necessarily high. Moreover, in the assessment of the effect of radiotherapy, [$^{18}$F]FDG must be used after at least 1 month of the therapy because transient increase in [$^{18}$F]FDG probably caused by inflammation is exhibited immediately after the therapy. Thus, [$^{18}$F]FDG is not suitable for use in the assessment of therapeutic effect. On the other hand, L-[$^{11}$C]Met is effective for the diagnosis of some tumors such as brain tumor and however, presents a problem of its low specificity to tumor itself.

Thus, an object of the present invention is to provide a labeled compound for positron imaging with high specificity to tumor and a labeled compound capable of early assessment of therapeutic effect.

Means to Solve the Problem

To attain the object, the present invention provides a radioactive tyrosine derivative represented by the formula (I) or a pharmaceutically acceptable salt thereof.

[Chemical formula 1]

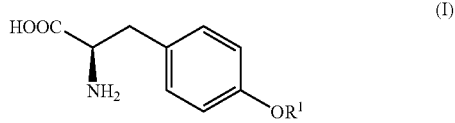

(I)

In the formula, R$^1$ represents a group selected from the group consisting of —$^{11}$CH$_3$, —$^{11}$CH$_2$CH$_3$, —CH$_2$$^{18}$F, and —CH$_2$CH$_2$CH$_2$$^{18}$F.

In this context, the compound wherein R$^1$ is —$^{11}$CH$_3$ is O—[$^{11}$C]methyl-D-tyrosine (hereinafter, abbreviated to D-[$^{11}$C]MT), and the compound wherein R$^1$ is —CH$_2$$^{18}$F is O—[$^{18}$F]fluoromethyl-D-tyrosine (hereinafter, abbreviated to D-[$^{18}$F]FMT). Alternatively, the compound wherein R$^1$ is —$^{11}$CH$_2$CH$_3$ is O—[$^{11}$C]ethyl-D-tyrosine (hereinafter, abbreviated to D-[$^{11}$C]ET), and the compound wherein R$^1$ is —CH$_2$CH$_2$CH$_2$$^{18}$F is O—[$^{18}$F]fluoropropyl-D-tyrosine (hereinafter, abbreviated to D-[$^{18}$F]FPT).

O—[$^{18}$F]fluoroethyl-D-tyrosine (hereinafter, abbreviated to D-[$^{18}$F]FET) represented by the formula (III) has already been known as a compound analogous to these radioactive tyrosine derivatives (see e.g., Non-Patent Documents 2 and 3).

[Chemical formula 2]

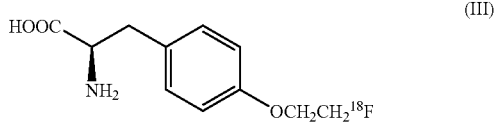

(III)

However, D-[$^{18}$F]FET has been thought to be not available in tumor imaging because it has low blood-brain barrier permeability and does not accumulate in tumor tissues due to its low uptake to cancer cells (see e.g., Non-Patent Documents 2 and 3).

However, the present inventors have found that the radioactive tyrosine derivative represented by the formula (I) or the pharmaceutically acceptable salt thereof sufficiently accumulates in tumor tissues in sharp contrast to the behavior described in Non-Patent Documents 2 and 3 and in addition, accumulates in a manner specific to tumor tissues, and have shown that it can be used as a labeled compound for PET.

The radioactive tyrosine derivative represented by the formula (I) or the pharmaceutically acceptable salt thereof that possesses such excellent properties may efficiently and steadily be obtained by alkylating or fluoroalkylating D-tyrosine.

The present invention also provides a labeled agent for positron imaging consisting of a radioactive tyrosine derivative represented by the formula (II) or a pharmaceutically acceptable salt thereof.

[Chemical formula 3]

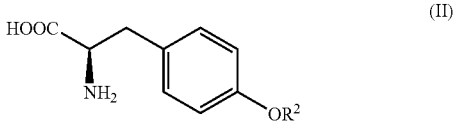

(II)

In the formula, $R^2$ represents any group selected from the group consisting of —$^{11}CH_3$, —$^{11}CH_2CH_3$, —$CH_2{}^{18}F$, —$CH_2CH_2{}^{18}F$, and —$CH_2CH_2CH_2{}^{18}F$.

Not only the radioactive tyrosine derivative represented by the formula (I) but also the radioactive tyrosine derivative represented by the formula (II) sufficiently accumulates in tumor tissues and in addition, accumulates in a manner specific to tumor tissues. Therefore, it can be used as a labeled compound for PET.

The present invention also provides an agent for assessing grade of tumor malignancy consisting of a radioactive tyrosine derivative represented by the formula (II) or a pharmaceutically acceptable salt thereof. The radioactive tyrosine derivative represented by the formula (II) or the pharmaceutically acceptable salt thereof differs in the degree of accumulation to tumor according to the tumor proliferation rate and as such, can also be used as an agent for assessing grade of tumor malignancy. Unlike [$^{18}$F]FDG, the radioactive tyrosine derivative represented by the formula (II) is hardly affected by inflammation and may therefore be used in the assessment of therapeutic effect immediately after therapy.

The present invention further provides a method for detecting tumor comprising: a step of administering a radioactive tyrosine derivative represented by the formula (II) or a pharmaceutically acceptable salt thereof to a subject; a step of measuring a radiation dose of each tissue of the subject; and a detection step of detecting a tissue with a relatively large radiation dose as a tumor tissue through comparisons of the radiation dose of each tissue. The radioactive tyrosine derivative represented by the formula (II) or the pharmaceutically acceptable salt thereof hardly accumulates in normal tissues and easily accumulates in tumor tissues. By use of this property, tumor may be detected. It is preferred that at the detection step, a tissue with a relatively large radiation dose with respect to the radiation dose of blood should be detected as a tumor tissue. This is because the difference between normal tissues and tumor tissues can be defined clearly by using the radiation dose of blood as a reference.

Effect of the Invention

A labeled agent for positron imaging with high specificity to tumor and a compound useful as a labeled agent capable of early assessment of therapeutic effect can be provided.

BRIEF DESCRIPTION OF THE DRAWINGS

FIG. 1 is a diagram showing the accumulating amounts of L- and D-[$^{11}$C]Met in each organ. FIG. 1(a) indicates the accumulating amount by SUV, and FIG. 1(b) indicates the accumulating amount by SUV (organ)/SUV (blood);

FIG. 2 is a diagram showing the accumulating amounts of L- and D-[$^{11}$C]MT in each organ. FIG. 2(a) indicates the accumulating amount by SUV, and FIG. 2(b) indicates the accumulating amount by SUV (organ)/SUV (blood);

FIG. 3 is a diagram showing the accumulating amounts of L- and D-[$^{18}$F]FMT in each organ. FIG. 3(a) indicates the accumulating amount by SUV, and FIG. 3(b) indicates the accumulating amount by SUV (organ)/SUV (blood);

DESCRIPTION OF REFERENCE NUMERAL

1: tumor site

BEST MODE FOR CARRYING OUT THE INVENTION

Figure 4:
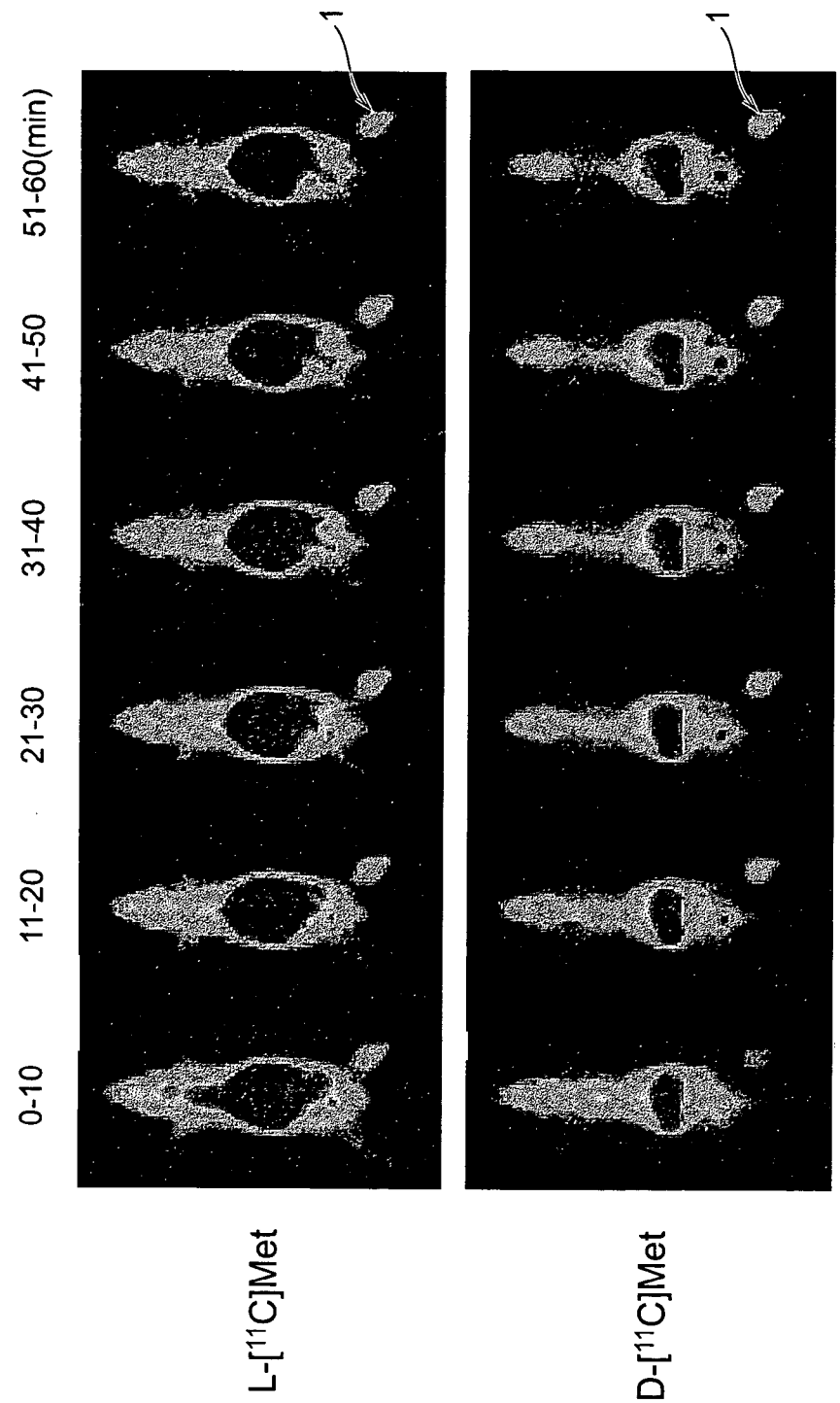
FIG. 4 is a diagram showing a result of planar imaging of L- and D-[$^{11}$C]Met administration in mice.

Hereinafter, the preferable embodiments of the present invention will be described in detail.

First, a radioactive tyrosine derivative of the present invention will be described. The radioactive tyrosine derivative of the present invention is represented by the formula (I). These derivatives sufficiently accumulate in tumor tissues and in addition, accumulate in a manner specific to tumor tissues. Therefore, they are useful as a labeled agent for positron imaging. Alternatively, these derivatives differ in the degree of accumulation to tumor according to the tumor proliferation rate and are therefore useful as an agent for assessing grade of tumor malignancy.

The compound represented by the formula (I) can be synthesized by alkylating or fluoroalkylating D-tyrosine. Hereinafter, a synthesis method thereof will be described by taking D-[$^{11}$C]MT and D-[$^{18}$F]FMT as an example.

D-[$^{11}$C]MT may be synthesized by [$^{11}$C]methylating D-tyrosine. Examples of reagents used in the methylation include: [$^{11}$C]methyl halide such as [$^{11}$C]methyl chloride, [$^{11}$C]methyl bromide, and [$^{11}$C]methyl iodide; and [$^{11}$C]methyl triflate. Among them, [$^{11}$C]methyl iodide and [$^{11}$C]methyl triflate are particularly preferable because D-[$^{11}$C]MT can be synthesized efficiently in a short time by virtue of their high reactivity. These reagents may be synthesized by a method known in the art (e.g., the method described in Journal of Labelled Compounds and Radiopharmaceuticals, Vol. 46, p. 555-566 (2003)).

A reaction solvent is not particularly limited as long as it dissolves the starting material therein without reacting therewith. For example, dimethyl sulfoxide may be used. After the termination of reaction, the crude product can be purified by reversed-phase HPLC to obtain D-[$^{11}$C]MT.

D-[$^{18}$F]FMT may be synthesized by [$^{18}$F]fluoromethylating D-tyrosine. Examples of reagents used in the fluoromethylation include [$^{18}$F]FCH$_2$Br and [$^{18}$F]fluoromethyl triflate. D-[$^{18}$F]FMT can be synthesized efficiently in a short time by virtue of the high reactivity of these reagents. These reagents may be synthesized by a method known in the art (e.g., the method described in Journal of Labelled Compounds and Radiopharmaceuticals, Vol. 46, p. 555-566 (2003)).

A reaction solvent is not particularly limited as long as it dissolves the starting material therein without reacting therewith. For example, dimethyl sulfoxide may be used. After the termination of reaction, the crude product can be purified by reverse-phase HPLC to obtain D-[$^{18}$F]FMT.

Likewise, D-[$^{11}$C]ET can be synthesized by [$^{11}$C]ethylating D-tyrosine with [$^{11}$C]ethyl iodide or the like. Alternatively, D-[$^{18}$F]FPT can be synthesized by [$^{18}$F]fluoropropylating D-tyrosine with [$^{18}$F]FCH$_2$CH$_2$CH$_2$OTs (Ts: p-toluenesulfonyl group) or the like.

Examples of a pharmaceutically acceptable salt of the radioactive tyrosine derivative of the present invention include alkali metal salts (e.g., sodium salts and potassium salts), calcium salts, and amine salts (e.g., diethylamine salts). Alternative examples thereof include hydrochloride, hydrobromide, sulfate and bisulfate, phosphate and hydrogenphosphate, acetate, citrate, fumarate, gluconate, lactate, maleate, succinate, and tartrate.

Next, a labeled agent for positron imaging of the present invention will be described. The labeled agent for positron imaging of the present invention consists of a radioactive tyrosine derivative represented by the formula (II) or a pharmaceutically acceptable salt thereof. These derivatives sufficiently accumulate in tumor tissues and in addition, accumulate in a manner specific to tumor tissues. Therefore, they are useful as a labeled agent for positron imaging.

The radioactive tyrosine derivative represented by the formula (II) may be synthesized by a method equivalent to the synthesis methods of D-[$^{11}$C]MT and D-[$^{18}$F]FMT. Alternatively, the method described in The Journal of Nuclear Medicine, Vol. 40, No. 1, pp. 205-212, 1999 may be utilized.

Examples of the pharmaceutically acceptable salt include alkali metal salts (e.g., sodium salts and potassium salts), calcium salts, and amine salts (e.g., diethylamine salts). Alternative examples thereof include hydrochloride, hydrogenbromide, sulfate and bisulfate, phosphate and hydrogenphosphate, acetate, citrate, fumarate, gluconate, lactate, maleate, succinate, and tartrate.

PET measurement using the radioactive tyrosine derivative represented by the formula (II) can be performed, for example, by administering the radioactive tyrosine derivative represented by the formula (II) to a subject and using a PET system (e.g., PPIS-4800 manufactured by Hamamatsu Photonics K. K.) to perform PET measurement. The PET system detects annihilation photons, that is, γ-rays, which are emitted by the binding between positrons released from the emitting nuclide ($^{11}$C or $^{18}$F) of the administered radioactive tyrosine derivative and surrounding substance-constituting electrons. Furthermore, the obtained measurement data may be processed, if necessary, with image reconstitution software to obtain an image.

The radioactive tyrosine derivative represented by the formula (II) accumulates in tumor tissues, whereas its accumulation to normal tissues is low. Therefore, the location of accumulation of the radioactive tyrosine derivative represented by the formula (II) can be determined by measuring the γ-ray level or by analyzing the image. As a result, it can be judged that tumor has been formed there.

Next, an agent for assessing grade of tumor malignancy of the present invention will be described. The agent for assessing grade of tumor malignancy of the present invention consists of a radioactive tyrosine derivative represented by the formula (II) or a pharmaceutically acceptable salt thereof. These derivatives differ in the degree of accumulation to tumor according to the tumor proliferation rate and are therefore useful as an agent for assessing grade of tumor malignancy.

The assessing grade of tumor malignancy using the radioactive tyrosine derivative represented by the formula (II) may be performed by the following procedures: the radioactive tyrosine derivative represented by the formula (II) is administered to a subject to perform PET measurement in the same way as in the method described above. The γ-ray level or image of a tumor site may be analyzed to assess the malignancy of the tumor. Namely, the radioactive tyrosine derivative represented by the formula (II) has the property of easily accumulating in tumor tissues with high proliferation rates. Therefore, the tumor, when having a high γ-ray level, can be judged as having high malignancy (high proliferation rate).

Therapeutic effect may be assessed by performing PET measurement using the agent for assessing grade of tumor malignancy of the present invention before and after therapy such as radiotherapy. Namely, when the γ-ray level of a tumor site is decreased after therapy, it can be judged that the therapy has suppressed the tumor proliferation rate and exerted sufficient therapeutic effect.

Finally, a method for detecting tumor of the present invention will be described. The method for detecting tumor of the present invention comprises: the step of administering a radioactive tyrosine derivative represented by the formula (II) or a pharmaceutically acceptable salt thereof to a subject; the step of measuring a radiation dose of each tissue of the subject; and the detection step of detecting a tissue with a relatively large radiation dose as a tumor tissue through comparison of the radiation dose of each tissue.

To detect tumor, the radioactive tyrosine derivative represented by the formula (II) is first administered to a subject. An administration method thereof is usually intravenous administration. Next, a radiation dose of each tissue of the subject is measured. The radiation dose measurement may be performed by the PET measurement described above. Then, a tissue with a relatively large radiation dose is detected as a tumor tissue through comparison of the radiation dose of each tissue. It is preferred that SUV (standardized uptake value), particularly SUV (tissue)/SUV (blood) (a relative value with respect to the radiation dose of blood), should be used in the comparison. Alternatively, a tissue with a relatively large radiation dose may be identified from an image.

EXAMPLES

Hereinafter, the present invention will be described in detail with reference to Examples. However, the present invention is not intended to be limited to these Examples.

Example 1

D-[$^{11}$C]MT Synthesis

At first, [$^{11}$C]methyl iodide was synthesized by the following method: a cyclotron was used to produce [$^{11}$C]carbon dioxide by bombarding a nitrogen gas filled to a target with proton beams (18 MeV, 20 μA). The produced [$^{11}$C]carbon dioxide was bubbled into a cooled tetrahydrofuran solution (0.5 mL) of 0.1 M lithium aluminum hydride to reduce the [$^{11}$C]carbon dioxide to [$^{11}$C]methanol. To this solution was added with 0.5 mL of hydroiodic acid to produce [$^{11}$C]methyl iodide.

D-tyrosine (1 mg) was supplemented with 10% sodium hydroxide aqueous solution (4.41 μl) and further with dimethyl sulfoxide (0.3 mL) to prepare a stock solution. The [$^{11}$C]methyl iodide produced by the method was bubbled into the stock solution and thereby trapped therein. Then, the reaction vessel was hermetically sealed, and reaction was performed at 80° C. for 3 minutes. The crude product was subjected to HPLC under conditions described below. A radioactive peak fraction with a retention time of 8 minutes was collected and concentrated under reduced pressure to purify D-[$^{11}$C]MT.

HPLC Conditions
Column: YMC-Pack ODS-A (10×250 mm) (YMC Co., Ltd.)
Mobile phase: ethanol:acetic acid:water=100:25:875
Flow rate: 4 mL/min
Detection wavelength: 280 nm The residue obtained by the concentration was redissolved in 3 mL of saline and sterilized by filtration with a 0.22-μm membrane filter to obtain a solution of 2 to 5 GBq of D-[$^{11}$C] MT in saline (radiochemical purity: 97% or higher).

Example 2

D-[$^{18}$F]FMT Synthesis

At first, [$^{18}$F]FCH$_2$Br was synthesized in the same way as in the method described in Radiation and Isotopes, Vol. 57, pp. 347-352, 2002.

D-tyrosine (1 mg) was supplemented with 10% sodium hydroxide aqueous solution (4.41 μl) and further with dimethyl sulfoxide (0.3 mL) to prepare a stock solution. The [$^{18}$F]FCH$_2$Br produced by the method was bubbled into the stock solution and thereby trapped therein. Then, the reaction vessel was hermetically sealed, and reaction was performed at 80° C. for 5 minutes. The crude product was subjected to HPLC under conditions described below. A radioactive peak fraction with a retention time of 9 minutes was collected and concentrated under reduced pressure to purify D-[$^{18}$F]FMT.

HPLC Conditions
Column: YMC-Pack ODS-A (10×250 mm) (YMC Co., Ltd.)
Mobile phase: ethanol:acetic acid:water=100:25:875
Flow rate: 4 mL/min
Detection wavelength: 280 nm The residue obtained by the concentration was redissolved in 3 mL of saline and sterilized by filtration with a 0.22-μm membrane filter to obtain a solution of 1 to 3 GBq of D-[$^{18}$F] FMT in saline (radiochemical purity: 97% or higher).

Comparative Example 1

O—[$^{11}$C]methyl-L-tyrosine (L-[$^{11}$C]MT) synthesis)

L-[$^{11}$C]MT was synthesized in the same way as in the method described in Example 1 except that L-tyrosine was used as a starting material instead of D-tyrosne.

Comparative Example 2

O—[$^{18}$F]fluoromethyl-L-tyrosine (D-[$^{18}$F]FMT) synthesis

L-[$^{18}$F]FMT was synthesized in the same way as in the method described in Example 2 except that L-tyrosine was used as a starting material instead of D-tyrosine.

Comparative Examples 3 to 7

Synthesis of additional known PET labeled compounds

L- and D-[$^{11}$C]Met (Comparative Examples 3 and 4) were synthesized by the method described in The Journal of Nuclear Medicine, Vol. 28, pp. 1037-1040, 1987. [$^{18}$F]FDG (Comparative Example 5) was synthesized by the method described in The Journal of Nuclear Medicine, Vol. 27, pp. 235-238, 1986. [$^{11}$C]choline (Comparative Example 6) was synthesized by the method described in The Journal of Nuclear Medicine, Vol. 38, pp. 842-847, 1997. 3'-deoxy-3'-[$^{18}$F]fluorothymidine ([$^{18}$F]FLT; Comparative Example 7) was synthesized by the method described in Journal of Radioanalytical and Nuclear Chemistry, Vol. 243, pp. 843-846, 2000.

Test Example 1

Measurement of organ distribution in cancer-bearing mice)

Human cervical cancer HeLa cells (cell strain: 15S3D) were subcutaneously transplanted at 5×10$^6$ cells/mouse to the thighs of 7-week-old nude mice (BALB/cA Jcl-nu, Clea Japan, Inc). After 2 weeks of the transplantation (9 weeks of age), the compounds of Examples 1 to 2 and the compounds of Comparative Examples 1 to 7 were administered through the tail veins at 10 MBq (the compounds of Example 1 and Comparative Examples 1, 3, 4, and 6) or 1 MBq (the compounds of Example 2 and Comparative Examples 2, 5, and 7). After 1 hour of the administration, the mice were decapitated to collect each organ (blood, heart, lung, liver, kidney, spleen, muscle, bone, small intestine, gastrointestinal tract, pancreas, brain, and tumor). The radioactivity of each organ was measured with an automatic gamma counter, and the weight of each organ was measured. SUV (standardized uptake value) that served as an index of the accumulating amounts of the administered compounds was determined. Furthermore, to correct the accumulating amounts, SUV (organ)/SUV (blood) was determined by dividing the SUV of each organ by the SUV of blood. The obtained results are shown in FIGS. 1 to 3.

FIG. 1 is a diagram showing the accumulating amounts of L- and D-[$^{11}$C]Met in each organ. FIG. 1(a) indicates the accumulating amount by SUV, and FIG. 1(b) indicates the accumulating amount by SUV (organ)/SUV (blood). As can be seen from the result shown in FIG. 1(b), the accumulation of L- and D-[$^{11}$C]Met was observed in the tumor and however, was also high in the normal tissues (particularly, liver, kidney, spleen, intestine, and pancreas). Thus, L- and D-[$^{11}$C] Met were shown to be unsuitable for tumor diagnosis because of their low specificity to tumor.

FIG. 2 is a diagram showing the accumulating amounts of L- and D-[$^{11}$C]MT in each organ. FIG. 2(a) indicates the accumulating amount by SUV, and FIG. 2(b) indicates the accumulating amount by SUV (organ)/SUV (blood). As can be seen from the result shown in FIG. 2(b), the accumulation of L- and D-[$^{11}$C]MT was observed in the tumor, whereas their accumulation was low in the normal tissues except for the pancreas and was specific to the tumor. Furthermore, the D-form had a higher value of SUV (organ: tumor)/SUV (blood) than the L-form. Moreover, the ratio of accumulation to the pancreas to accumulation to the tumor indicated by SUV (organ)/SUV (blood) was shown to be lower in the D-form than in the L-form. Thus, it was suggested that the D-form can be utilized as an excellent tumor diagnostic agent as compared with the L-form.

FIG. 3 is a diagram showing the accumulating amounts of L- and D-[$^{18}$F]FMT in each organ. FIG. 3(a) indicates the accumulating amount by SUV, and FIG. 3(b) indicates the accumulating amount by SUV (organ)/SUV (blood). As can be seen from the result shown in FIG. 3(b), the accumulation of L- and D-[$^{11}$C]MT was observed in the tumor, whereas their accumulation was low in the normal tissues except for the pancreas and was specific to the tumor. Furthermore, the D-form had a higher value of SUV (organ: tumor)/SUV (blood) than the L-form and was shown to have particularly high specificity to the tumor. Thus, it was suggested that the D-form can be utilized as an excellent tumor diagnostic agent as compared with the L-form.

Test Example 2

Planar measurement in cancer-bearing mice

Nude mice (BALB/cA Jcl-nu) into which HeLa had been transplanted in the same way as in Test Example 1 were administered through the tail veins with the compounds of Examples 1 to 2 and the compounds of Comparative Examples 1 to 7 at 2.5 MBq. Measurement was performed (1 minute×60 frames) for 60 minutes immediately after the compound administration by use of a planar imaging system (PPIS-4800 manufactured by Hamamatsu Photonics K. K.) and indicated by images each comprising 10 frames integrated. The results obtained by the planar measurement of each administered compound are shown in FIGS. 4 to 6.

FIG. 4 is a diagram showing a result of planar measurement of L- and D-[$^{11}$C]Met administered. The accumulation of both the L- and D-forms was observed in the tumor site and however, was significantly stronger in the normal tissues. Thus, they were shown to be unsuitable for tumor imaging.

Figure 5:
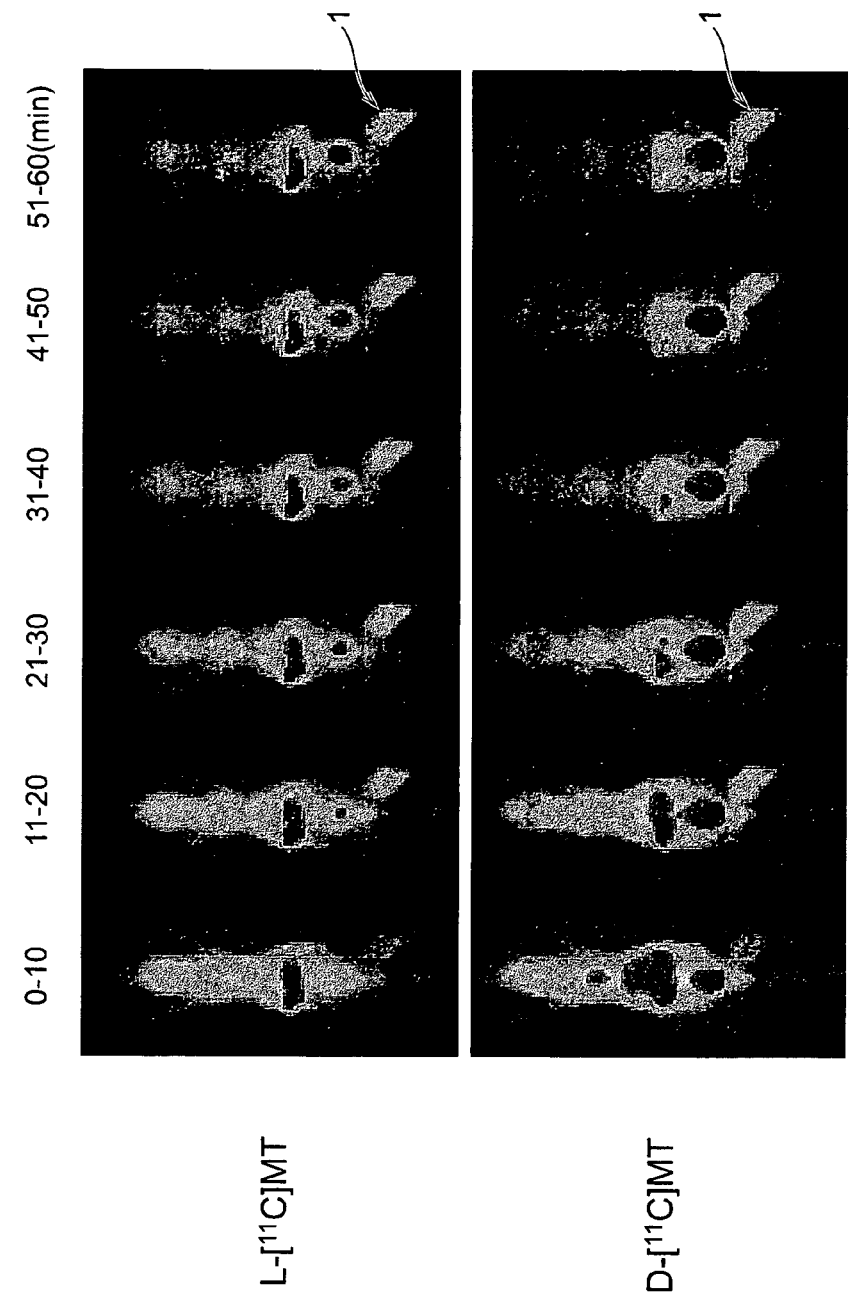
FIG. 5 is a diagram showing a result of planar imaging of L- and D-[$^{11}$C]MT administration in mice.

FIG. 5 is a diagram showing a result of planar measurement of L- and D-[$^{11}$C]MT administered. The accumulation of both the L- and D-forms was observed in the tumor site. Moreover, the D-form was confirmed to accumulate in a manner specific to the tumor as compared with the L-form.

Figure 6:
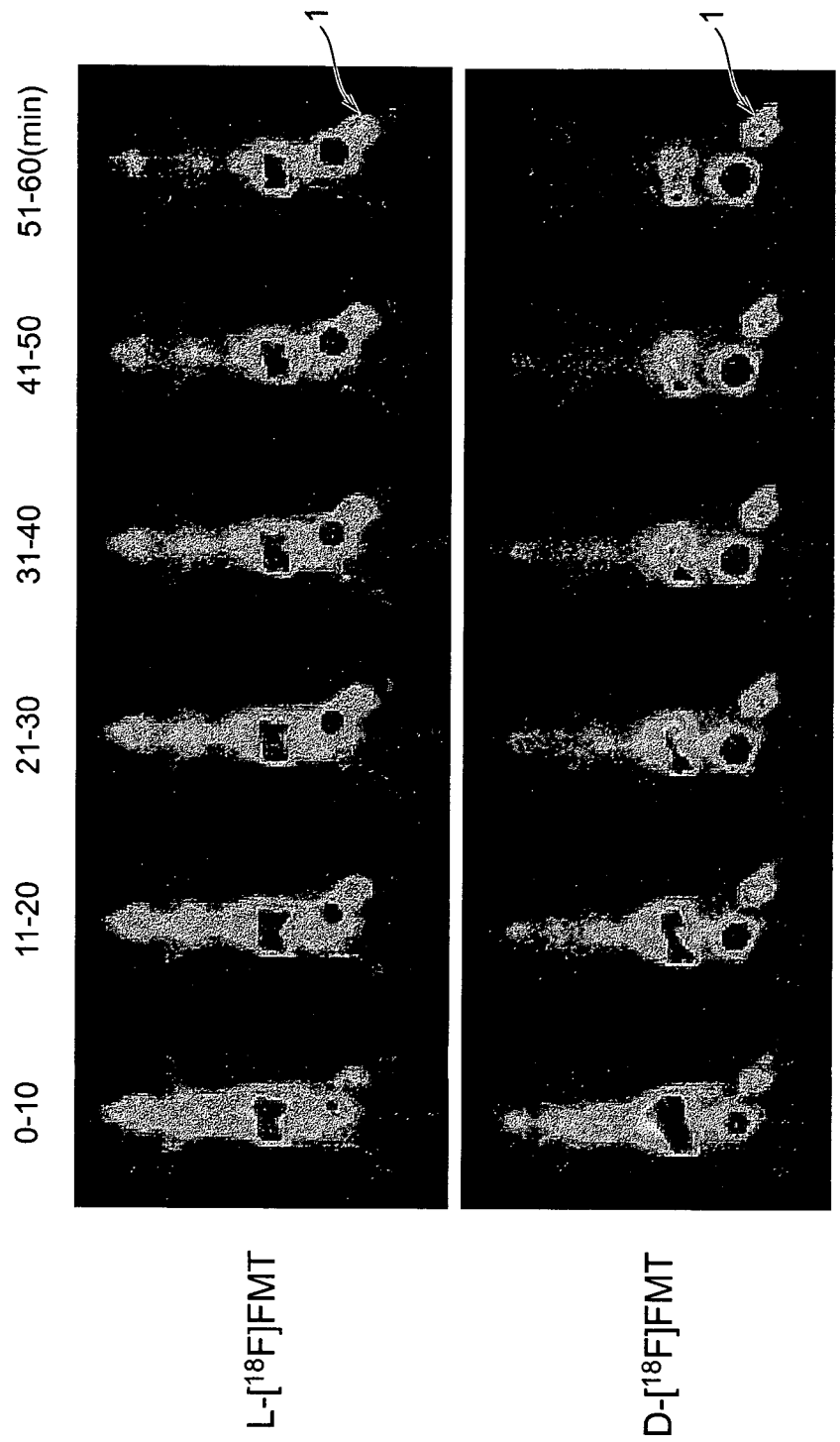
FIG. 6 is a diagram showing a result of planar imaging of L- and D-[$^{18}$F]FMT administration in mice.

FIG. 6 is a diagram showing a result of planar measurement of L- and D-[$^{18}$F]FMT administered. The accumulation of both the L- and D-forms was observed in the tumor site. Moreover, the D-form was confirmed to accumulate in a manner specific to the tumor as compared with the L-form.

Test Example 3

Figure 7:
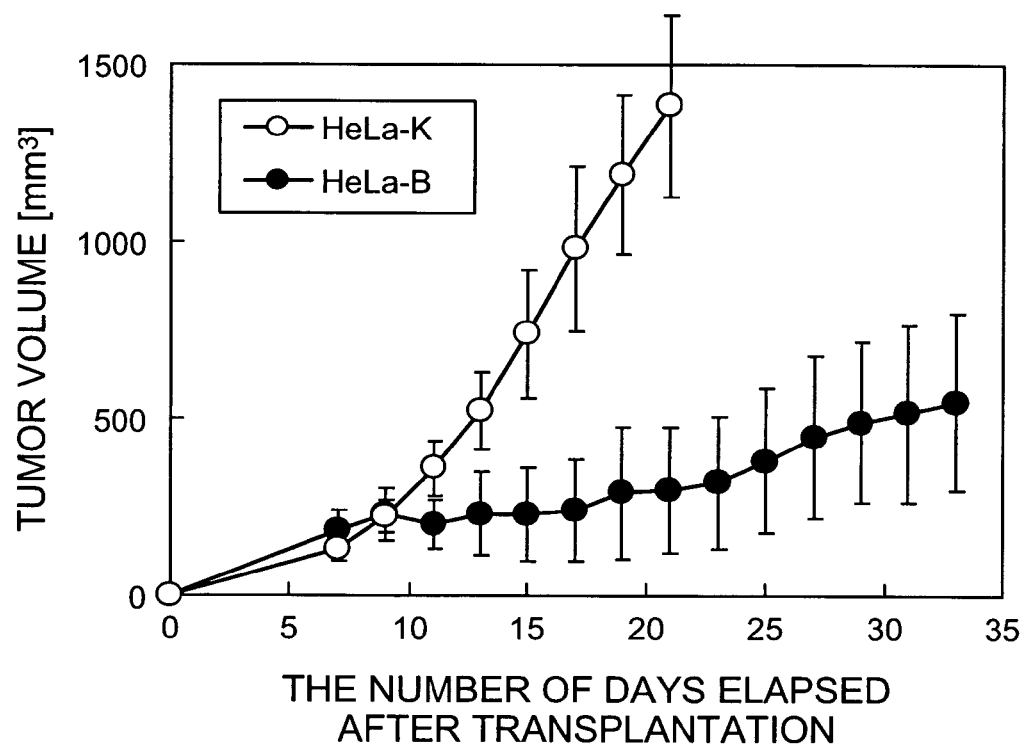
FIG. 7 is a diagram showing the relationship between the number of days elapsed after HeLa transplantation and tumor volumes.

Relationship between tumor proliferation rate and degree of accumulation of labeled compound for positron imaging HeLa cells differing in cell growth rate were transplanted to nude mice (BALB/cA Jcl-nu) to examine the accumulation to tumor of the compounds of Examples 1 to 2 and the compounds of Comparative Examples 1 to 7 administered to the mice. HeLa-K (cell strain: 15S3D) and HeLa-B (Health Science Research Resources Bank: JCRB9004) were subcutaneously transplanted at 5×10$^6$ cells/mouse and 2×10$^7$ cells/mouse, respectively, to the thighs of female BALB/cA Jcl-nu nude mice (HeLa-K: 7-week-old mice, HeLa-B: 5-week-old mice). The HeLa-K- and HeLa-B-transplanted mice, when becoming 9 week old after 2 weeks and 4 weeks of the transplantation, respectively, were used in the experiment. To examine the relationship between the accumulation of each labeled compound in the cancer-bearing mice and the proliferation rate of the tumor tissue, tumor size was daily measured. Doubling time (DT) was calculated according to the calculation formula: DT=t×log2 (V1/V0) proposed by Schwartz, wherein t denotes the number of days required for the tumor volume to reach V1 (mm$^3$) from V0 (mm$^3$), and the volume (mm$^3$) was calculated according to ½×length (mm)× width$^2$ (mm$^2$) from the major axis of the tumor. FIG. 7 is a graph showing the relationship between the number of days elapsed after HeLa transplantation and tumor volumes. As can be seen from FIG. 7, HeLa-K was a cancer cell that had a high proliferation rate, while HeLa-B was a cancer cell that had a low proliferation rate. The doubling times of HeLa-K and HeLa-B calculated from FIG. 7 were 4.4 days and 11.0 days, respectively.

The HeLa-K- and HeLa-B-transplanted nude mice were administered through the tail veins with [$^{18}$F]FDG, [$^{11}$C] choline, [$^{18}$F]FLT, L- and D-[$^{11}$C]Met, and L- and D-[$^{11}$C] MT at 1 MBq ([$^{18}$F]FDG and [$^{18}$F]FLT) or 10 MBq ([$^{11}$C] choline, L- and D-[$^{11}$C]Met, and L- and D-[$^{11}$C]MT). After 1 hour of the administration, the mice were decapitated to collect blood and tumor. The radioactivities of the blood and tumor were measured with an automatic gamma counter, their weights were measured, and SUV was determined. Furthermore, to correct the accumulating amounts, SUV (organ)/ SUV (blood) was determined by dividing the SUV of the tumor by the SUV of the blood. The obtained results are shown in FIGS. 8 to 9.

Figure 8:
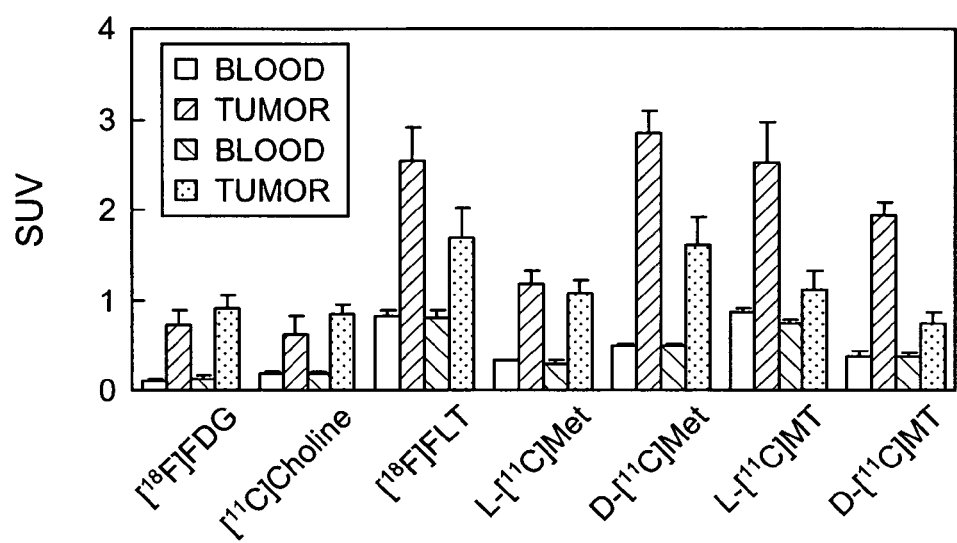
FIG. 8 is a diagram showing the accumulating amount (SUV) of each compound in blood and tumor.
Figure 9:
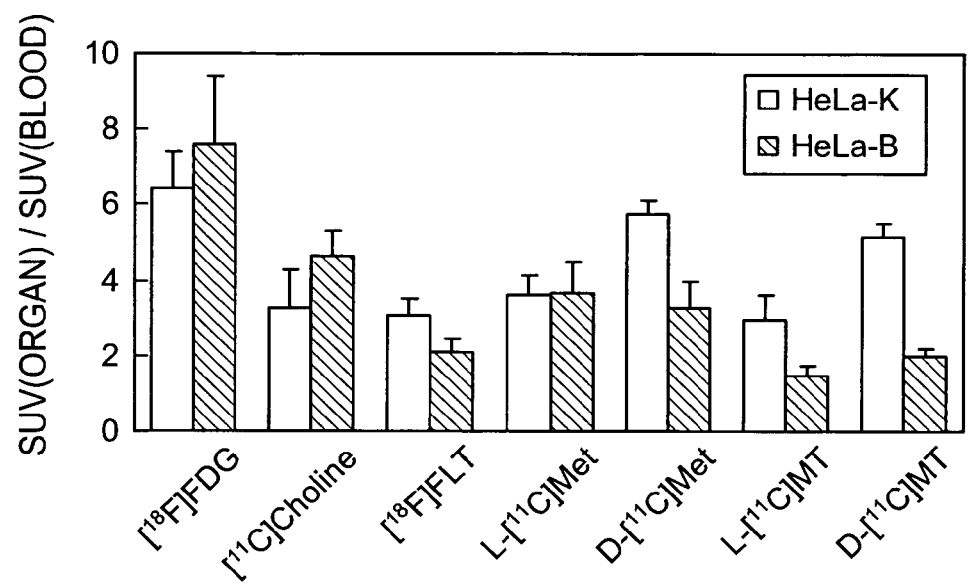
FIG. 9 is a diagram showing the accumulating amount (SUV (organ)/SUV (blood)) of each compound in tumor.

FIGS. 8 and 9 are respectively diagrams showing the accumulating amount of each compound in blood and tumor. FIG. 8 indicates the accumulating amount by SUV, and FIG. 9 indicates the accumulating amount by SUV (organ)/SUV (blood). As can be seen from the result shown in FIG. 9, D-[$^{11}$C]MT accumulated more in HeLa-K exhibiting faster proliferation. The difference in the degree of accumulation depending on the difference in proliferation rate was remarkably large for D-[$^{11}$C]MT as compared with L-[$^{11}$C]MT and D-[$^{11}$C]Met. For [$^{18}$F]FDG and L-[$^{11}$C]Met, the difference in the degree of accumulation depending on the difference in proliferation rate was not detected.

The detection of the difference in proliferation rate that can be achieved depending on the difference in the degree of accumulation suggests that when a tumor proliferation rate was decreased by the manifestation of therapeutic effect, this change can be grasped. Thus, D-[$^{11}$C]MT is considered to be excellent for the assessment of therapeutic effect on tumor as compared with existing labeled compounds.

Example 3

D-[$^{11}$C]ET Synthesis

At first, [$^{11}$C]ethyl iodide was synthesized in the same way as in the method described in Applied Radiation and Isotopes, Vol. 50, pp. 693-697, 1999.

D-tyrosine (1 mg) was supplemented with 10% sodium hydroxide aqueous solution (4.41 µl) and further with dimethyl sulfoxide (0.3 mL) to prepare a material solution. The [$^{11}$C]ethyl iodide produced by the method was bubbled into the material solution and thereby trapped therein. Then, the reaction vessel was hermetically sealed, and reaction was performed at 80° C. for 3 minutes. The crude product was subjected to HPLC under conditions described below. A radioactive peak fraction with a retention time of 13 minutes was collected and concentrated under reduced pressure to purify D-[$^{11}$C]ET.

HPLC Conditions
Column: YMC-Pack ODS-A (10×250 mm) (YMC Co., Ltd.)
Mobile phase: ethanol:acetic acid:water=120:25:855
Flow rate: 4 mL/min
Detection wavelength: 280 nm The residue obtained by the concentration was redissolved in 3 mL of saline and sterilized by filtration with a 0.22-µm membrane filter to obtain a solution of 0.8 to 1.5 GBq of D-[$^{11}$C]ET in saline (radiochemical purity: 99% or higher).

Example 4

D-[$^{18}$F]FET Synthesis

At first, [$^{18}$F]FCH$_2$CH$_2$OTs was synthesized in the same way as in the method described in Synapse, Vol. 54, pp. 37-45, 2004.

D-tyrosine (3 mg) was supplemented with 10% sodium hydroxide aqueous solution (13.2 µl) and further with dimethyl sulfoxide (0.3 mL) to prepare a material solution. The material solution was added to the [$^{18}$F]FCH$_2$CH$_2$OTs produced by the method. Then, the reaction vessel was hermetically sealed, and reaction was performed at 125° C. for 10 minutes. The crude product was subjected to HPLC under conditions described below. A radioactive peak fraction with a retention time of 9 minutes was collected and concentrated under reduced pressure to purify D-[$^{18}$F]FET.

HPLC Conditions
Column: YMC-Pack ODS-A (10×250 mm) (YMC Co., Ltd.)
Mobile phase: ethanol:acetic acid:water=100:25:875
Flow rate: 4 mL/min
Detection wavelength: 280 nm The residue obtained by the concentration was redissolved in 3 mL of saline and sterilized by filtration with a 0.22-µm membrane filter to obtain a solution of 0.5 to 2 GBq of D-[$^{18}$F]FET in saline (radiochemical purity: 99% or higher).

Example 5

D-[$^{18}$F]FPT Synthesis

At first, [$^{18}$F]FCH$_2$CH$_2$CH$_2$OTs was synthesized with TsOCH$_2$CH$_2$CH$_2$OTs as a material in the same way as in the method described in Synapse, Vol. 54, pp. 37-45, 2004.

D-tyrosine (3 mg) was supplemented with 10% sodium hydroxide aqueous solution (13.2 µl) and further with dimethyl sulfoxide (0.3 mL) to prepare a material solution. The material solution was added to the [$^{18}$F]FCH$_2$CH$_2$CH$_2$OTs produced by the method. Then, the reaction vessel was hermetically sealed, and reaction was performed at 125° C. for 10 minutes. The crude product was subjected to HPLC under conditions described below. A radioactive peak fraction with a retention time of 17 minutes was collected and concentrated under reduced pressure to purify D-[$^{18}$F]FPT.

HPLC Conditions
Column: YMC-Pack ODS-A (10×250 mm) (YMC Co., Ltd.)
Mobile phase: ethanol:acetic acid:water=120:25:855
Flow rate: 4 mL/min
Detection wavelength: 280 nm The residue obtained by the concentration was redissolved in 3 mL of saline and sterilized by filtration with a 0.22-µm membrane filter to obtain a solution of 0.2 to 0.6 GBq of D-[$^{18}$F]FPT in saline (radiochemical purity: 99% or higher).

Comparative Example 8

O—[$^{11}$C]Ethyl-L-tyrosine (L-[$^{11}$C]ET) Synthesis

L-[$^{11}$C]ET was synthesized in the same way as in the method described in Example 3 except that L-tyrosine was used as a material instead of D-tyrosine.

Comparative Example 9

O—[$^{18}$F]Fluoroethyl-L-tyrosine (L-[$^{18}$F]FET) Synthesis

L-[$^{18}$F]FET was synthesized in the same way as in the method described in Example 4 except that L-tyrosine was used as a material instead of D-tyrosine.

Comparative Example 10

O—[$^{18}$F]Fluoropropyl-L-tyrosine (L-[$^{18}$F]FPT) Synthesis

L-[$^{18}$F]FPT was synthesized in the same way as in the method described in Example 5 except that L-tyrosine was used as a material instead of D-tyrosine.

Test Example 4

Measurement of organ distribution in cancer-bearing mice

The organ distribution of the compounds of Examples 3 to 5 and Comparative Examples 8 to 10 was measured in the same way as in Test Example 1. The obtained results are shown in FIGS. 10 to 12.

Figure 10:
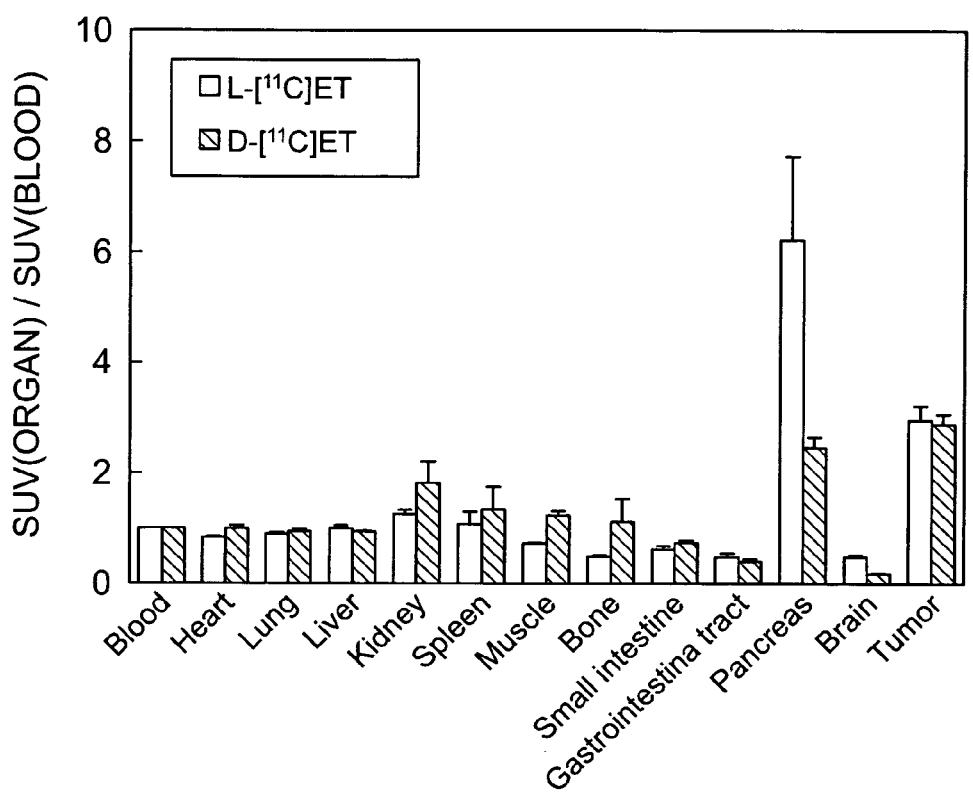
FIG. 10 is a diagram showing the accumulating amounts of L- and D-[$^{11}$C]ET in each organ. The accumulating amount is indicated by SUV (organ)/SUV (blood)

FIG. 10 is a diagram showing the accumulating amounts of L- and D-[$^{11}$C]ET in each organ. The accumulating amount is indicated by SUV (organ)/SUV (blood). As can be seen from this result, the accumulation of L- and D-[$^{11}$C]ET was observed in the tumor, whereas their accumulation was low in the normal tissues except for the pancreas and was specific to the tumor. Furthermore, the D-form had a similar value of SUV (organ: tumor)/SUV (blood) comparable to that of the L-form. Moreover, the ratio of accumulation to the pancreas to accumulation to the tumor indicated by SUV (organ)/SUV (blood) was shown to be lower in the D-form than in the L-form. Thus, it was suggested that the D-form can be utilized as an excellent tumor diagnostic agent as compared with the L-form.

Figure 11:
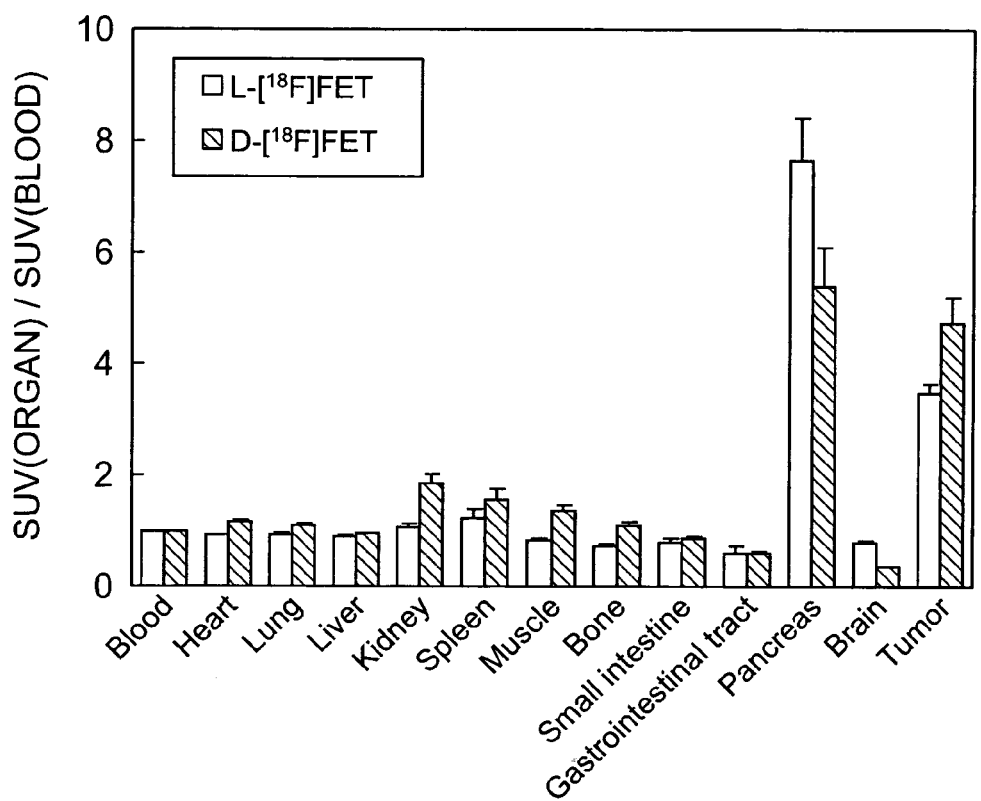
FIG. 11 is a diagram showing the accumulating amounts of L- and D-[$^{18}$F]FET in each organ. The accumulating amount is indicated by SUV (organ)/SUV (blood)

FIG. 11 is a diagram showing the accumulating amounts of L- and D-[$^{18}$F]FET in each organ. The accumulating amount is indicated by SUV (organ)/SUV (blood). As can be seen from this result, the accumulation of L- and D-[$^{18}$F]FET was observed in the tumor, whereas their accumulation was low in the normal tissues except for the pancreas and was specific to the tumor. Furthermore, the D-form had a higher value of SUV (organ: tumor)/SUV (blood) than the L-form and was shown to have particularly high specificity to the tumor. Moreover, the ratio of accumulation to the pancreas to accumulation to the tumor indicated by SUV (organ)/SUV (blood) was shown to be lower in the D-form than in the L-form. Thus, it was suggested that the D-form can be utilized as an excellent tumor diagnostic agent as compared with the L-form.

Figure 12:
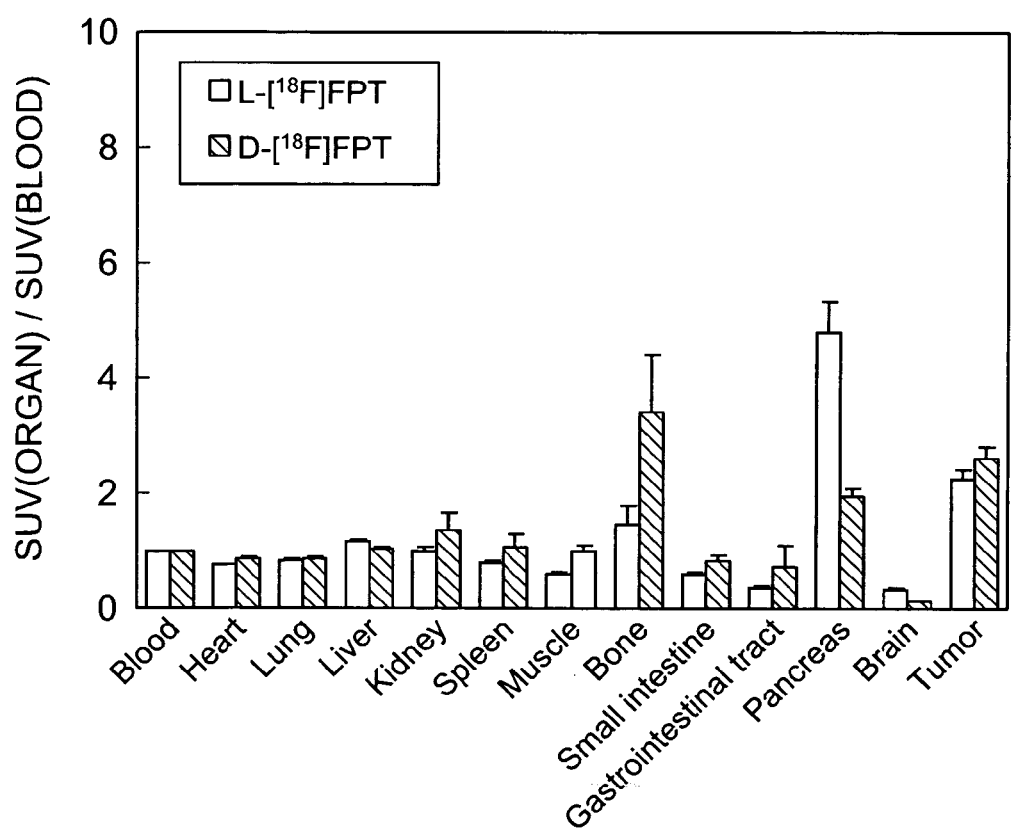
FIG. 12 is a diagram showing the accumulating amounts of L- and D-[$^{18}$F]FPT in each organ. The accumulating amount is indicated by SUV (organ)/SUV (blood)

FIG. 12 is a diagram showing the accumulating amounts of L- and D-[$^{18}$F]FPT in each organ. The accumulating amount is indicated by SUV (organ)/SUV (blood). As can be seen from this result, the accumulation of L- and D-[$^{18}$F]FPT was observed in the tumor, whereas their accumulation was low in the normal tissues except for the pancreas and bone and was specific to the tumor. Furthermore, the D-form had a similar value of SUV (organ: tumor)/SUV (blood) comparable to that of the L-form. Moreover, the ratio of accumulation to the pancreas to accumulation to the tumor indicated by SUV (organ)/SUV (blood) was shown to be lower in the D-form than in the L-form. Thus, it was suggested that the D-form can be utilized as an excellent tumor diagnostic agent as compared with the L-form.

Test Example 5

Relationship between tumor proliferation rate and degree of accumulation of labeled compound for positron imaging HeLa-K- and HeLa-B-transplanted nude mice were administered through the tail veins with L- and D-[$^{11}$C]ET, L- and D-[$^{18}$F]FMT, L-and D-[$^{18}$F]FET, and L- and D-[$^{18}$F]FPT at 10 MBq (L- and D-[$^{11}$C]ET) or 1 MBq (the others). After 1 hour of the administration, the mice were decapitated to collect blood and tumor. The radioactivities of the blood and tumor were measured with an automatic gamma counter, their weights were measured, and SUV was determined. Furthermore, to correct the accumulating amounts, SUV (organ)/SUV (blood) was determined by dividing the SUV of the tumor by the SUV of the blood. The obtained result is shown in FIG. 13.

Figure 13:
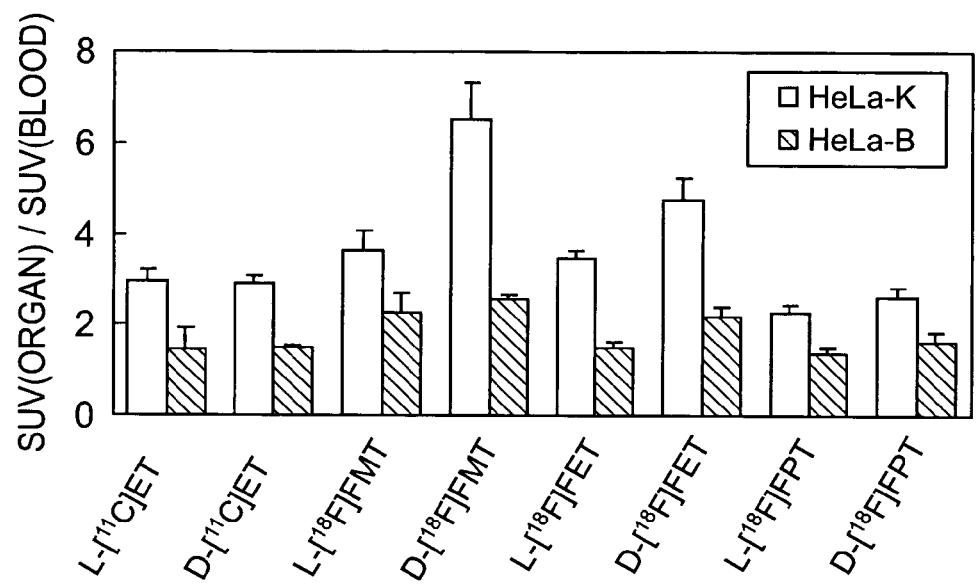
FIG. 13 is a diagram showing the accumulating amount (SUV (organ)/SUV (blood)) of each compound in tumor.

FIG. 13 is a diagram showing the accumulating amount of each compound in tumor. The accumulating amount is indicated by SUV (organ)/SUV (blood). As can be seen from this result, all of the compounds accumulated more in HeLa-K exhibiting faster proliferation. The difference in the degree of accumulation of D-[$^{18}$F]FMT depending on the difference in proliferation rate was remarkably large as compared with L-[$^{18}$F]FMT. Thus, these compounds are considered to be excellent for the assessment of therapeutic effect on tumor as compared with existing labeled compounds.

INDUSTRIAL APPLICABILITY

The present invention allows for tumor diagnosis by PET and particularly allows for the early assessment of the therapeutic effect of radiotherapy and so on.

The invention claimed is:

1. A radioactive tyrosine derivative represented by the formula (I) or a pharmaceutically acceptable salt thereof:

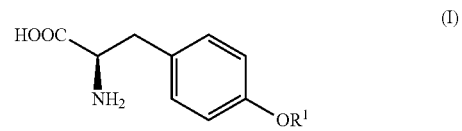

(I)

wherein $R^1$ represents a group selected from the group consisting of —$^{11}CH_3$, —$^{11}CH_2C_3$, —$CH_2{}^{18}F$, and —$CH_2CH_2CH_2{}^{18}F$.

* * * * *